(12) United States Patent
Wolfe et al.

(10) Patent No.: US 9,844,444 B2
(45) Date of Patent: Dec. 19, 2017

(54) FAR LATERAL SPACER

(75) Inventors: Steve Wolfe, Eagan, MN (US); James Schwender, Minneapolis, MN (US); Joeseph Gleason, Eagan, MN (US); Dan McPhillips, Ham Lake, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 13/557,993

(22) Filed: Jul. 25, 2012

(65) Prior Publication Data

US 2013/0079882 A1 Mar. 28, 2013

Related U.S. Application Data

(60) Provisional application No. 61/511,502, filed on Jul. 25, 2011.

(51) Int. Cl.
| | |
|---|---|
| *A61F 2/44* | (2006.01) |
| *A61F 2/46* | (2006.01) |
| *A61F 2/28* | (2006.01) |
| *A61F 2/30* | (2006.01) |

(52) U.S. Cl.
CPC ........... *A61F 2/4455* (2013.01); *A61F 2/4611* (2013.01); *A61F 2002/2835* (2013.01); *A61F 2002/30462* (2013.01); *A61F 2002/30471* (2013.01); *A61F 2002/30507* (2013.01); *A61F 2002/30561* (2013.01); *A61F 2002/30579* (2013.01); *A61F 2002/30581* (2013.01)

(58) Field of Classification Search
CPC ........................ A61F 2/4455; A61F 2002/4635
USPC ........................................................ 623/17.16
See application file for complete search history.

(56) References Cited

U.S. PATENT DOCUMENTS

| | | | |
|---|---|---|---|
| 8,506,635 B2* | 8/2013 | Palmatier et al. | 623/17.15 |
| 8,512,409 B1* | 8/2013 | Mertens et al. | 623/17.16 |
| 8,685,095 B2* | 4/2014 | Miller et al. | 623/17.11 |
| 2009/0275890 A1* | 11/2009 | Leibowitz et al. | 604/104 |
| 2009/0306671 A1* | 12/2009 | McCormack et al. | 606/90 |
| 2011/0301712 A1* | 12/2011 | Palmatier et al. | 623/17.16 |
| 2012/0059470 A1* | 3/2012 | Weiman | 623/17.11 |
| 2012/0215313 A1* | 8/2012 | Saidha et al. | 623/17.16 |
| 2013/0158664 A1* | 6/2013 | Palmatier et al. | 623/17.16 |
| 2014/0067071 A1* | 3/2014 | Weiman et al. | 623/17.16 |
| 2014/0100660 A1* | 4/2014 | Morgenstern Lopez et al. | 623/17.16 |

* cited by examiner

*Primary Examiner* — Ellen C Hammond
(74) *Attorney, Agent, or Firm* — Skaar Ulbrich Macari, P.A.

(57) ABSTRACT

A PEEK spacer for use in the spine is disclosed. The PEEK spacer may be configured to fit through Kambin's Triangle and expand upon insertion.

20 Claims, 17 Drawing Sheets

FAR LATERAL SPACER

PRIORITY

This application claims the benefit of U.S. Provisional Application Ser. No. 61/511,502, filed on Jul. 25, 2011, which is hereby incorporated by reference in its entirety herein.

FIELD

The present invention generally relates to a PEEK spacer for use in the spine. More particularly, the present invention relates to a PEEK spacer configured to fit through Kambin's Triangle and expand upon insertion.

SUMMARY

It is desirable to spare the facet joint when placing spacers for intervertebral stabilization, support and fusion. There is a need for a PEEK spacer that is small enough to fit through Kambin's Triangle, yet able to expand upon insertion to fully support and/or stabilize the intervertebral space. According to one embodiment of the present invention, the PEEK spacer may be placed via a facet sparing, transforaminal approach. In an embodiment, the PEEK spacer of the present invention may be placed through a minimally invasive operative access. In another embodiment, the PEEK spacer of the present invention may be placed through a percutaneous operative access.

According to one embodiment of the present invention, the PEEK spacer may be sized to be placed through a 15 mm×6 mm area at the L4-L5 vertebra. According to another aspect, the PEEK spacer of the present invention may be placed at any other desired vertebral level. In another embodiment of the present invention, the PEEK spacer may contain bone graft. According to one aspect, the PEEK spacer of the present invention may include an opening for bone graft insertion. In yet another embodiment of the present invention, the PEEK spacer may be configured to allow bony ingrowth through the spacer. According to one aspect of the present invention, the PEEK spacer may include an anti-backout feature.

In yet another embodiment, the PEEK spacer of the present invention may be configured to rotate from a first insertion position to a second implanted position. In an embodiment of the present invention, the PEEK spacer may be inserted in a first collapsed geometry and expanded to a second geometry after placement. In one embodiment of the present invention, the PEEK spacer may include arms, wings or other expandable members. In an embodiment of the present invention, expandable members may be solid such that fill material cannot escape back out of the entrance hole. In another embodiment expandable members may include slots or slits to allow bone ingrowth.

According to one embodiment of the present invention, the PEEK spacer may include a PEEK film configured to maintain the spacer in a collapsed geometry. In one aspect of the present invention, an expansion tool may be configured to pierce the PEEK film allowing the arms, wings or other expandable members to expand.

In yet another embodiment, the PEEK spacer of the present invention may be expanded using a screw or other suitable mechanism. According to another aspect of the present invention, the PEEK spacer may employ a ramp mechanism for expansion.

In an embodiment of the present invention, the PEEK spacer may include a central strut having a diversion configured to split a stream of bone or other fill material directing the fill material to both sides of the strut.

In yet another embodiment of the present invention, the arms, wings or other expandable members may be pivotally or otherwise movably attached to the spacer body. According to one aspect of the present invention, the PEEK spacer may include an asymmetrical taper along the implant width. In another embodiment, the PEEK spacer of the present invention may include lateral support features to help the implant stay upright when the disc space is subjected to shear forces.

According to one embodiment, a mesh container may be used with the PEEK spacer to contain fill material.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
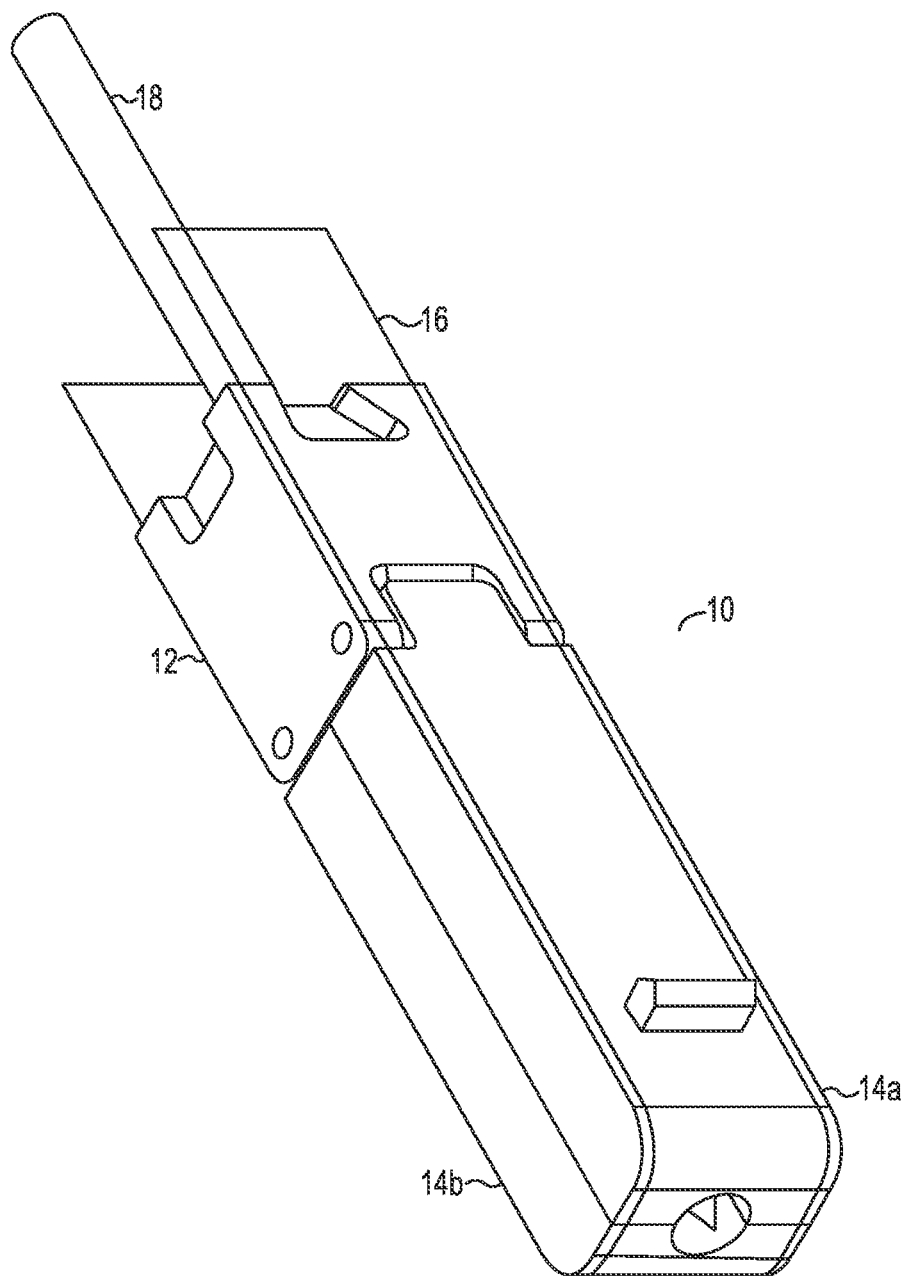
FIG. 1 depicts a perspective view of an embodiment of the present invention.
Figure 2:
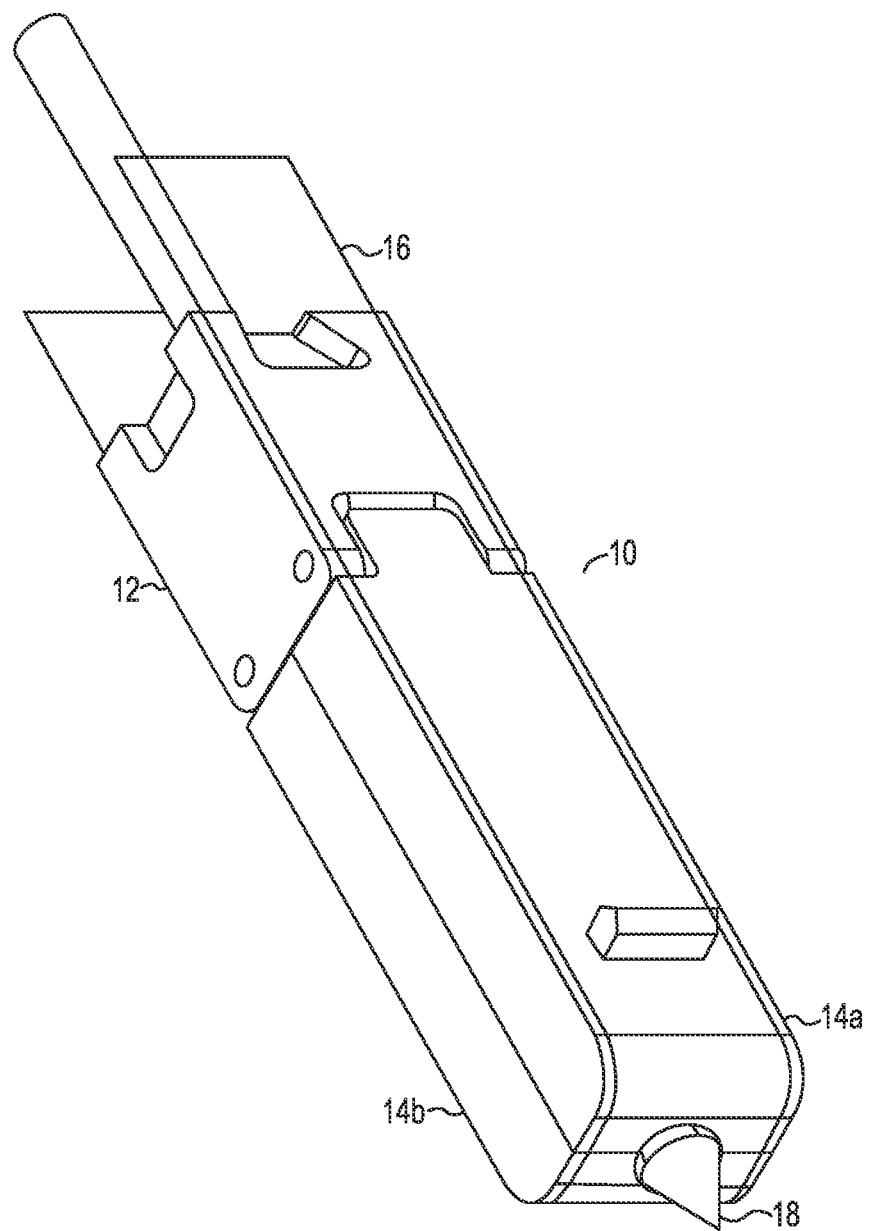
FIG. 2 depicts a perspective view of an embodiment of the present invention.
Figure 3:
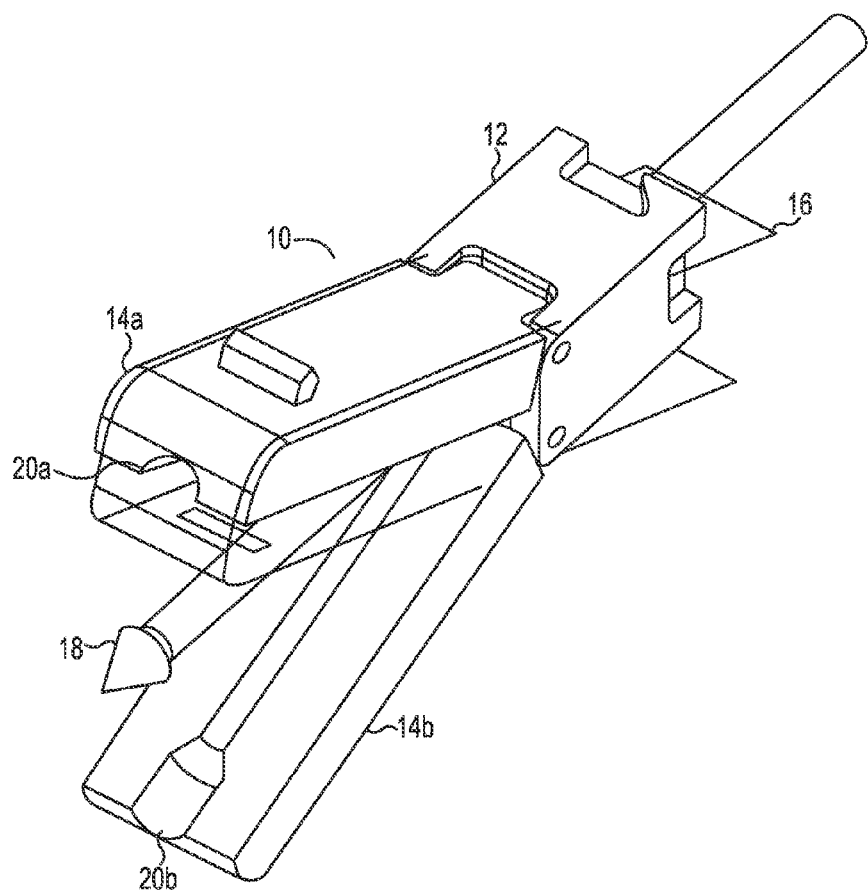
FIG. 3 depicts a perspective view of an embodiment of the present invention in an expanded configuration.
Figure 4:
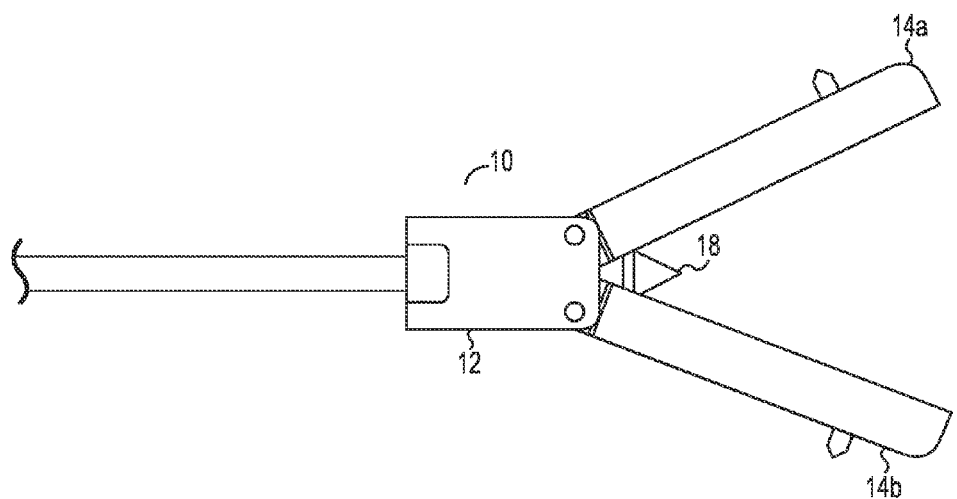
FIG. 4 depicts a side perspective view of an embodiment of the present invention in an expanded configuration.
Figure 5:
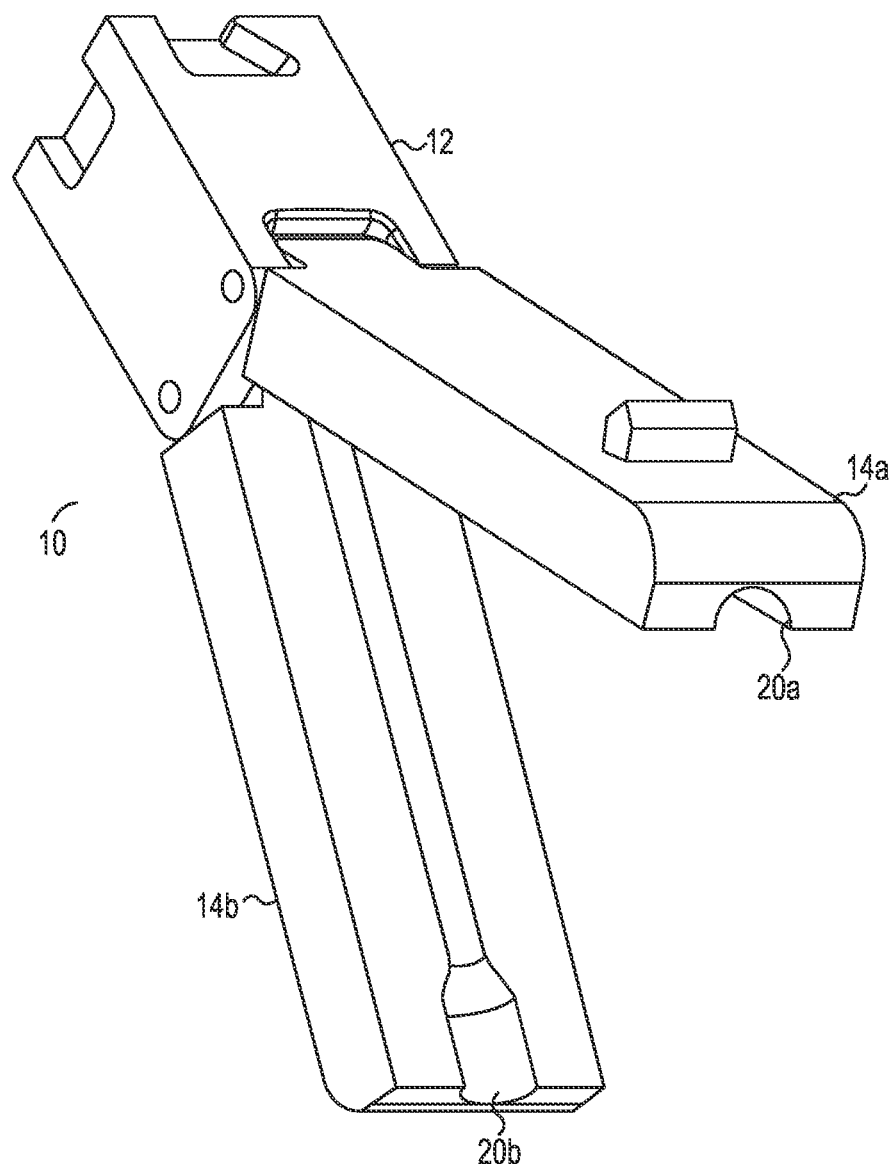
FIG. 5 depicts a perspective view of an embodiment of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

As shown in FIGS. 1-5, an embodiment of the present invention may include spacer body 12 and expandable members 14a and 14b. According to an embodiment of the present invention, the spacer of the present invention may be inserted into an intervertebral disc space while sparing the facet joint. The spacer of the present invention is sized to fit through Kambin's triangle via a far lateral surgical approach thus sparing the facet joint.

Expandable members 14a and 14b may be movably attached to spacer body 12. Peek or other suitable film 16 may be wrapped around spacer 10 such that spacer 10 remains in a collapsed geometry during insertion. In another embodiment, any thin thread, woven tape or other suitable material may be wrapped around spacer 10 such that spacer 10 remains in a collapsed geometry during insertion.

After placement of spacer 10 is complete, expansion tool 18 may be inserted through channels 20a and 20b such that tool 18 pierces film 16 allowing spacer 10 to be expanded into its expanded configuration. In an embodiment, film 16 may be pulled to expand spacer 10. Spacer 10 may be rotated once placed. Bone graft or other desired bone substitute or fill material, may be inserted through an opening in spacer 10.

Figure 6:
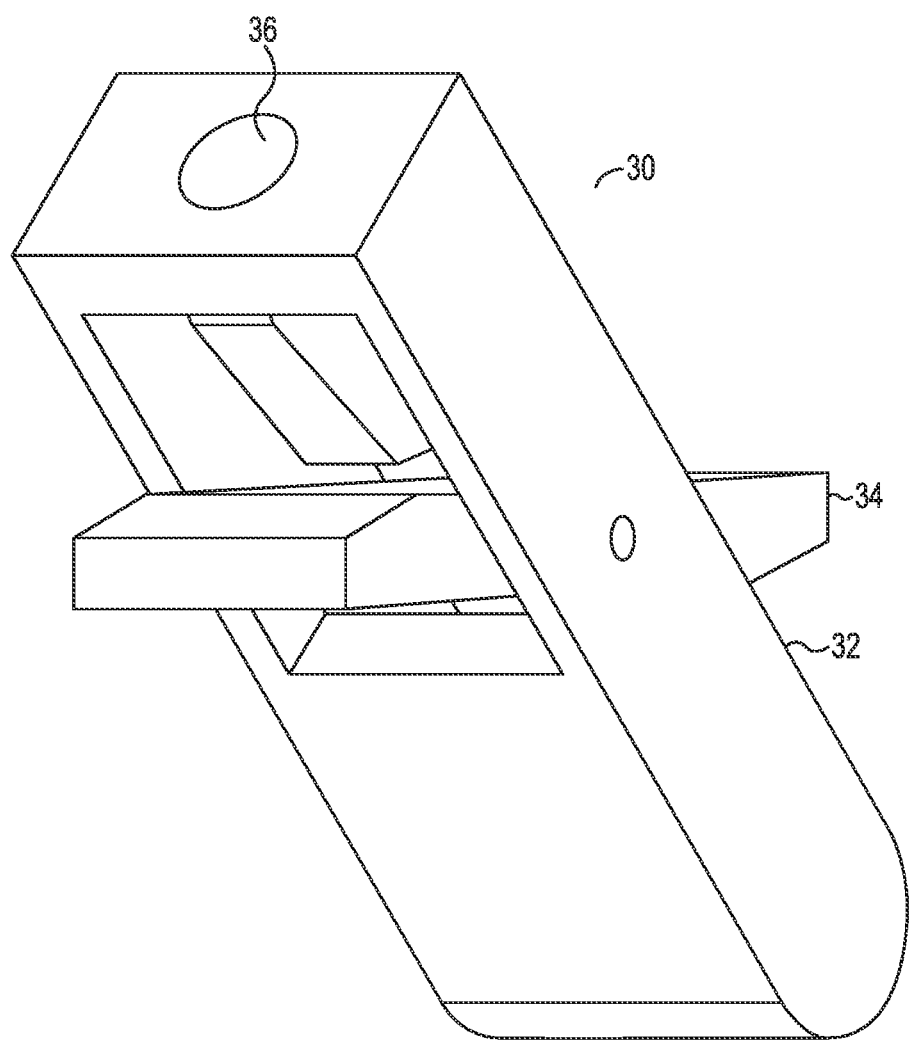
FIG. 6 depicts a perspective view of an embodiment of the present invention.

FIG. 6 depicts another embodiment of spacer 30 having spacer body 32 and expandable member 34. Opening 36 may accept the introduction of fill material.

Figure 7:
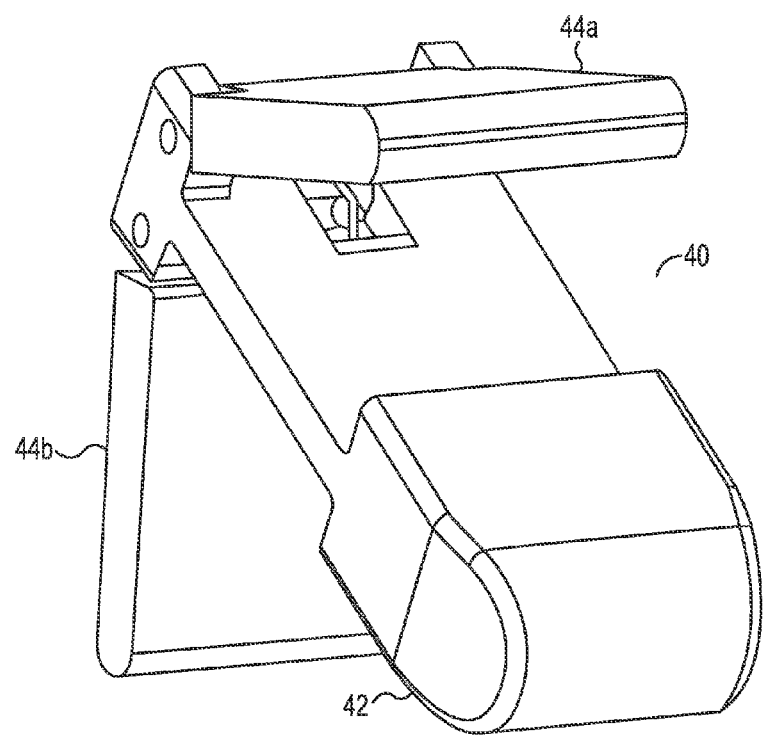
FIG. 7 depicts a perspective view of an embodiment of the present invention.

FIG. 7 depicts an alternate embodiment of spacer 40 having spacer body 42 and expandable members 44a and 44b.

Figure 8:
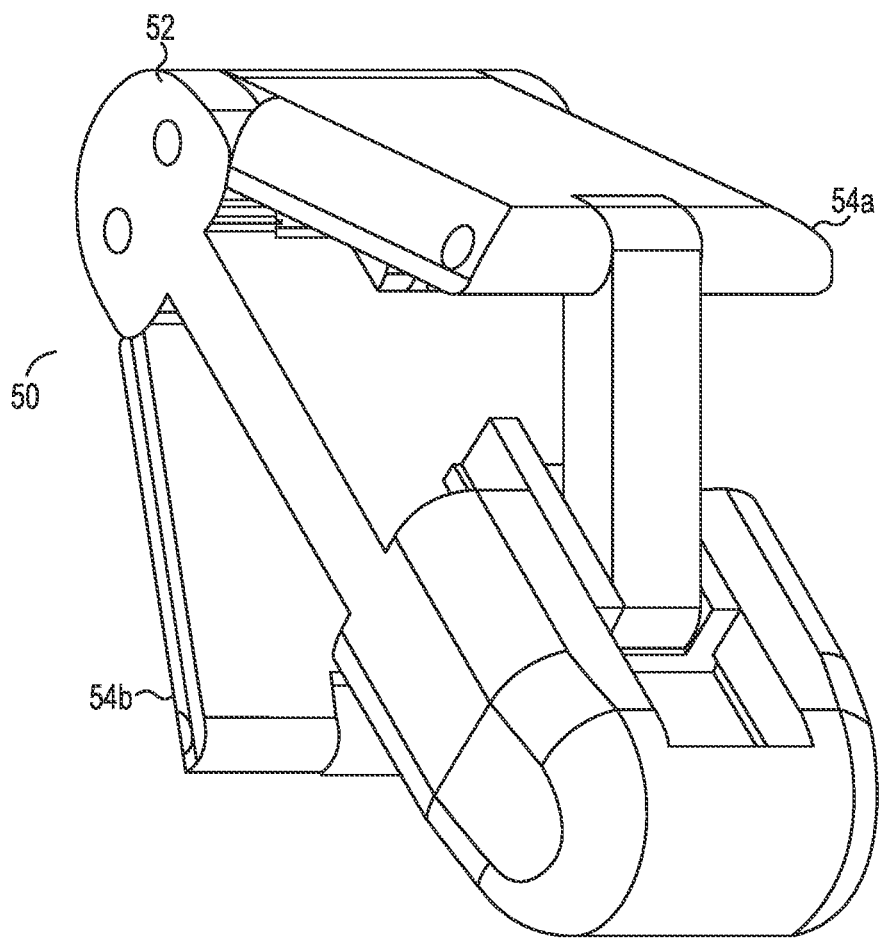
FIG. 8 depicts a perspective view of an embodiment of the present invention.

FIG. 8 depicts another embodiment of spacer 50 having spacer body 52 and expandable members 54a and 54b.

Figure 9:
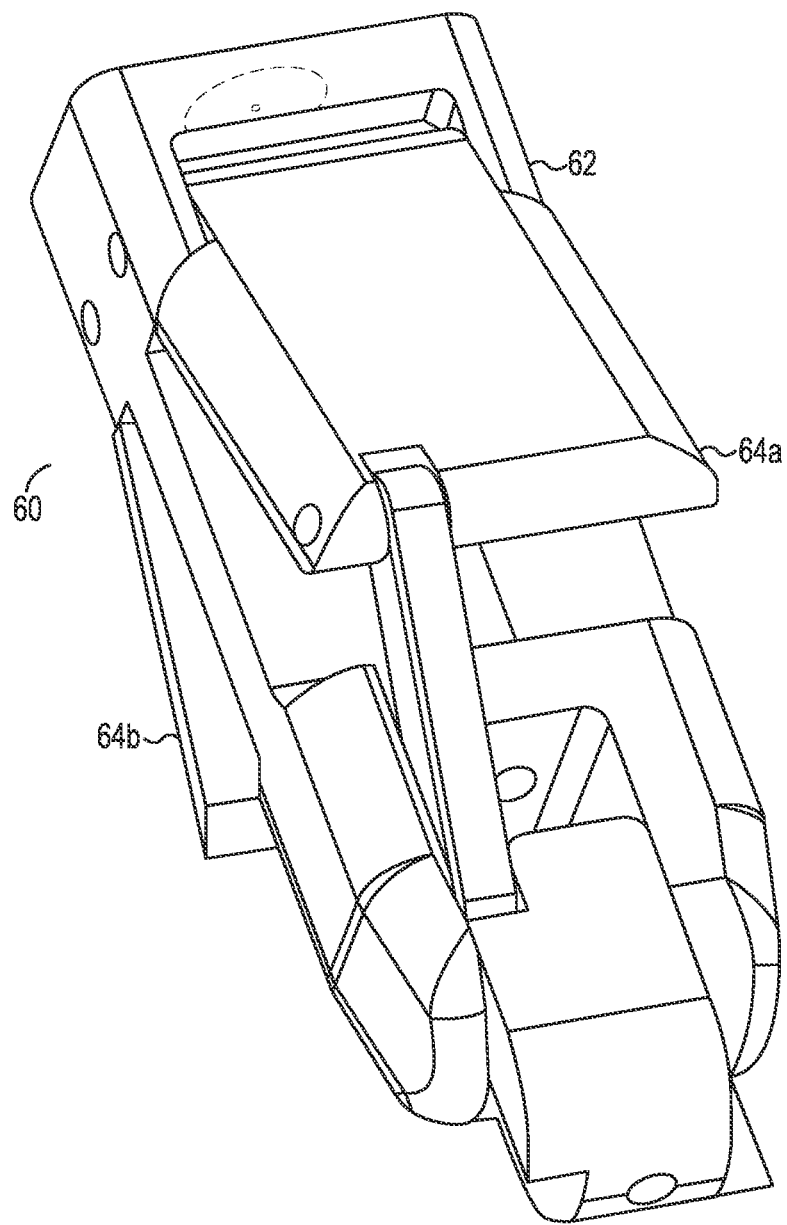
FIG. 9 depicts a perspective view of an embodiment of the present invention.

FIG. 9 depicts an embodiment of spacer 60 having spacer body 62 and expandable members 64a and 64b.

Figure 10:
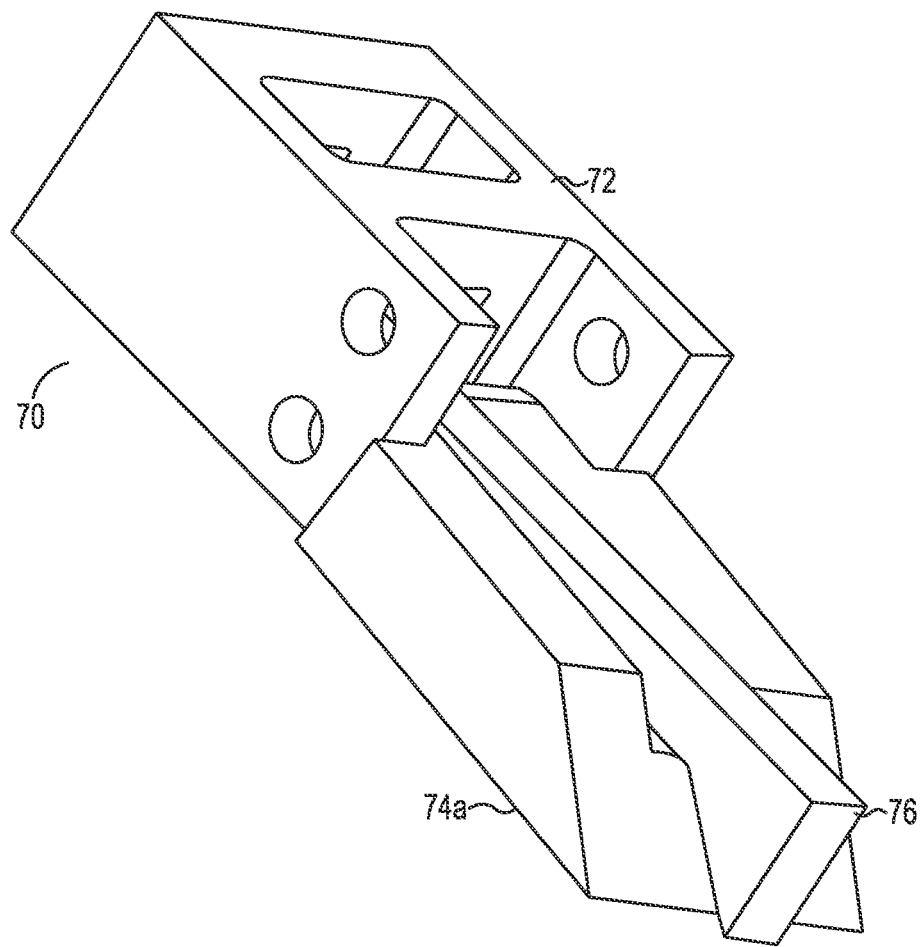
FIG. 10 depicts a perspective view of an embodiment of the present invention.

FIG. 10 depicts an embodiment of spacer 70 having spacer body 72, wherein only one expandable member 74a is shown to illustrate ramp 76.

Figure 11:
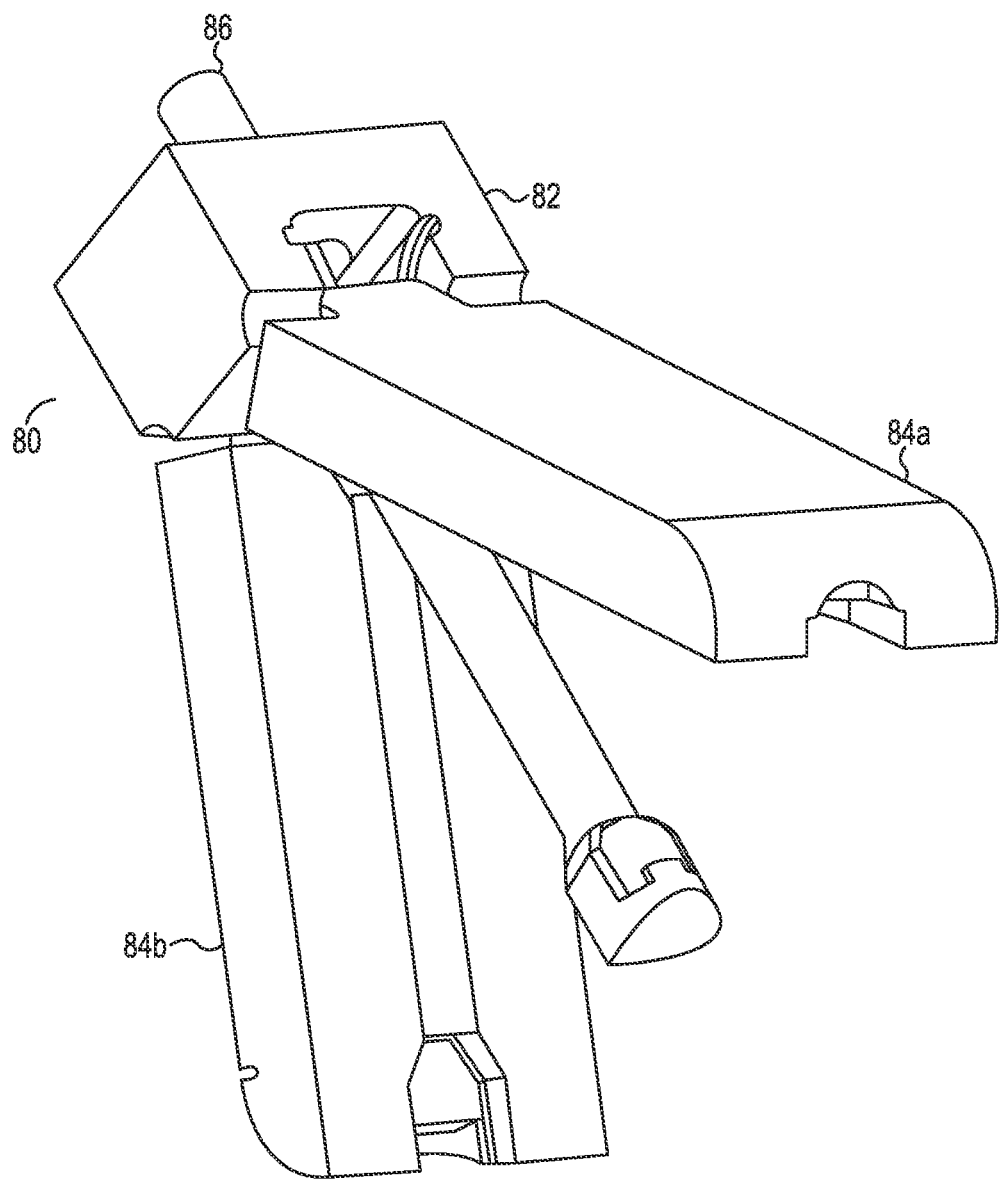
FIG. 11 depicts a perspective view of an embodiment of the present invention.

FIG. 11 depicts spacer 80 having spacer body 82 and expandable members 84a and 84b. Spacer 80 is shown in the expanded position illustrating expansion tool 86.

Figure 12:
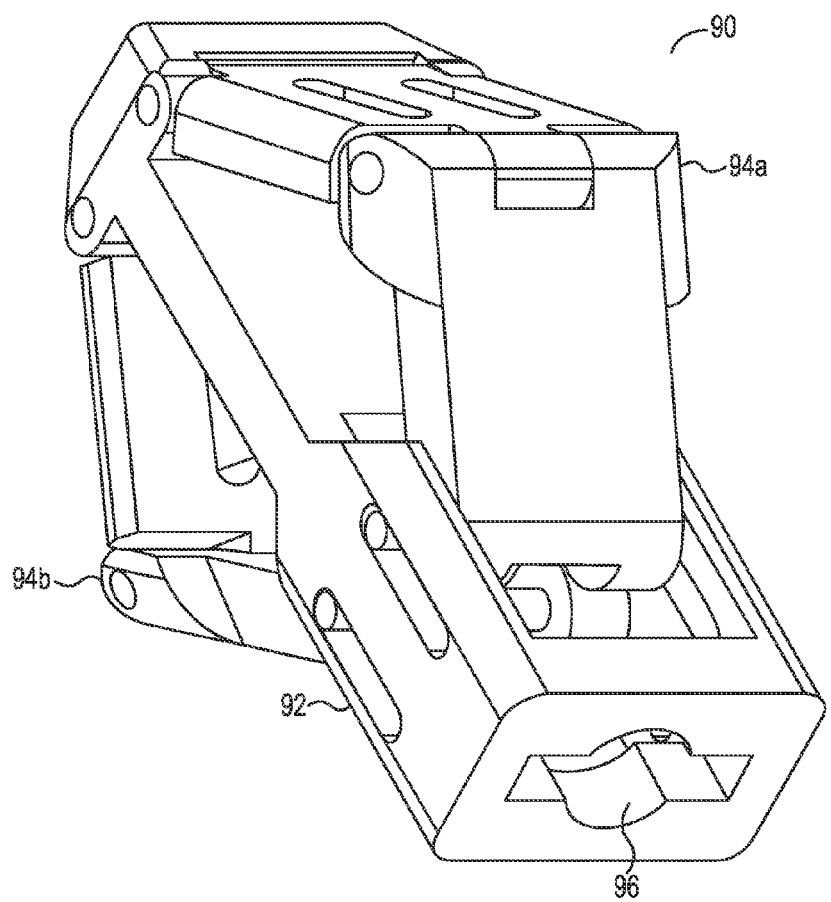
FIG. 12 depicts a perspective view of an embodiment of the present invention.

FIG. 12 depicts an alternate embodiment of spacer 90 having spacer body 92 and expandable members 94a and 94b. Opening 96 may accept the introduction of fill material.

Figure 13:
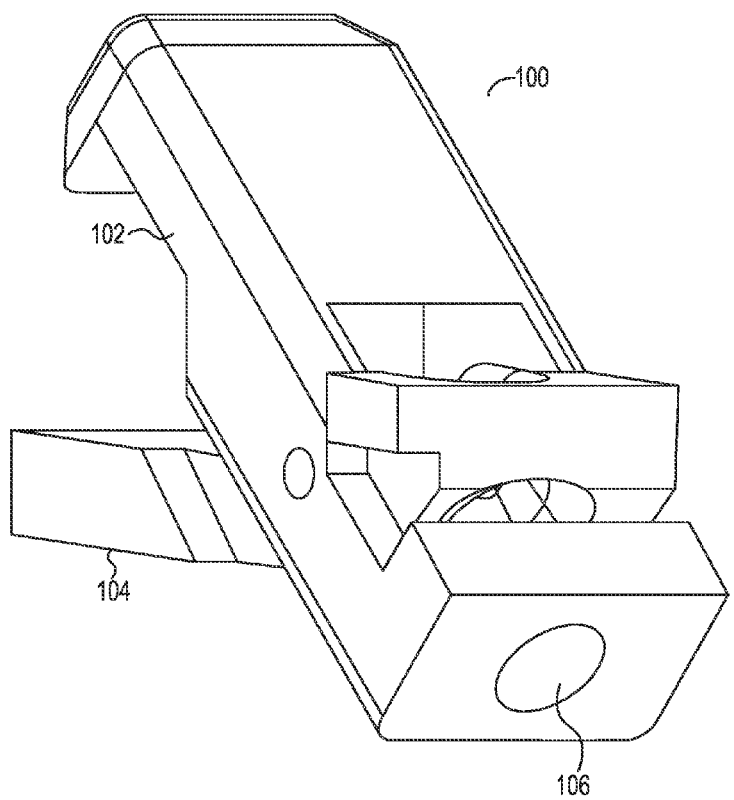
FIG. 13 depicts a perspective view of an embodiment of the present invention.

FIG. 13 depicts another embodiment of spacer 100 having spacer body 102 and an expandable member 104. Opening 106 may accept the introduction of fill material.

Figure 14:
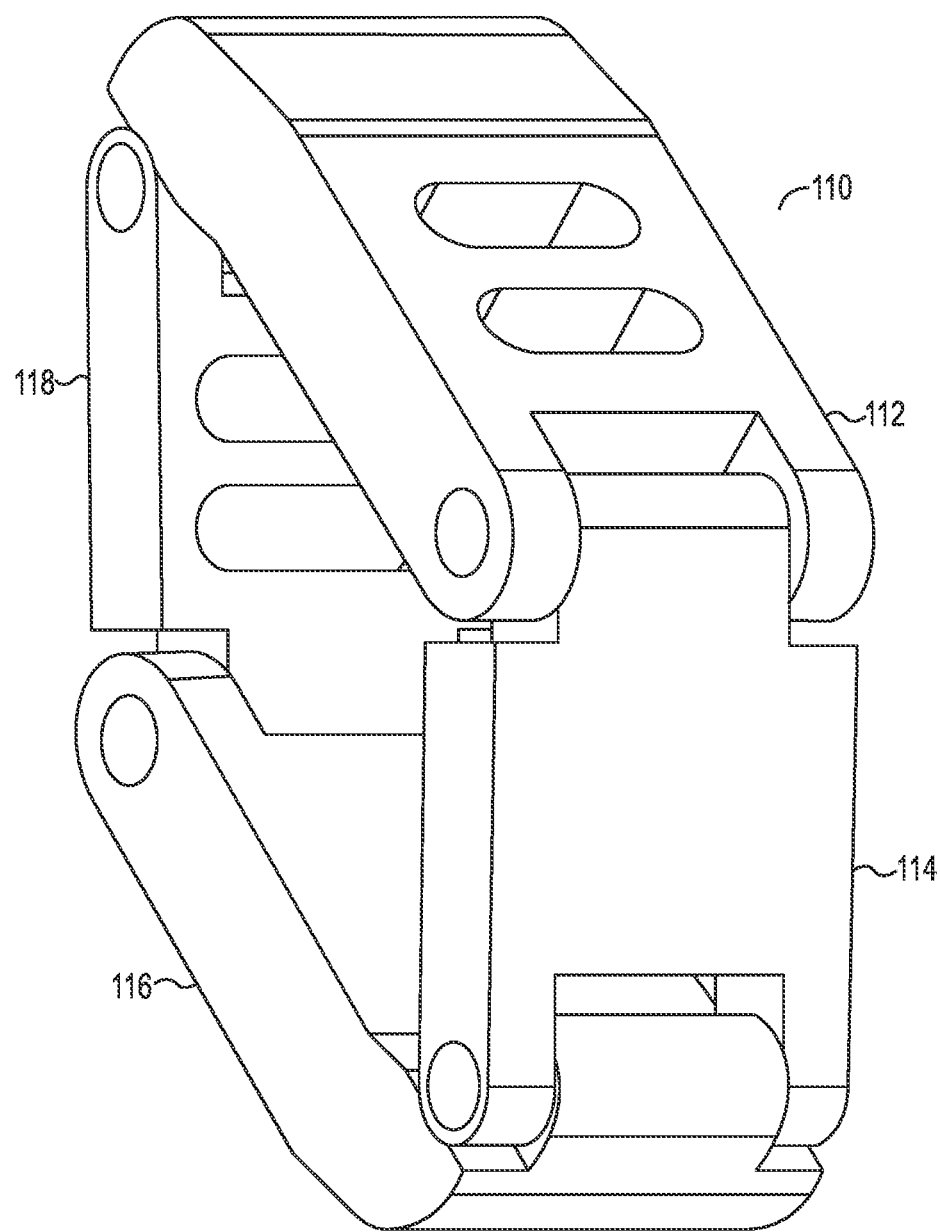
FIG. 14 depicts a perspective view of an embodiment of the present invention.

FIG. 14 depicts an alternate embodiment of spacer 110 having expandable members 112, 114, 116, and 118. Expandable members 112, 114, 116, and 118 are movably connected to one another such that spacer 110 may be inserted in a collapsed geometry and opened to an expanded geometry after placement.

Figure 15:
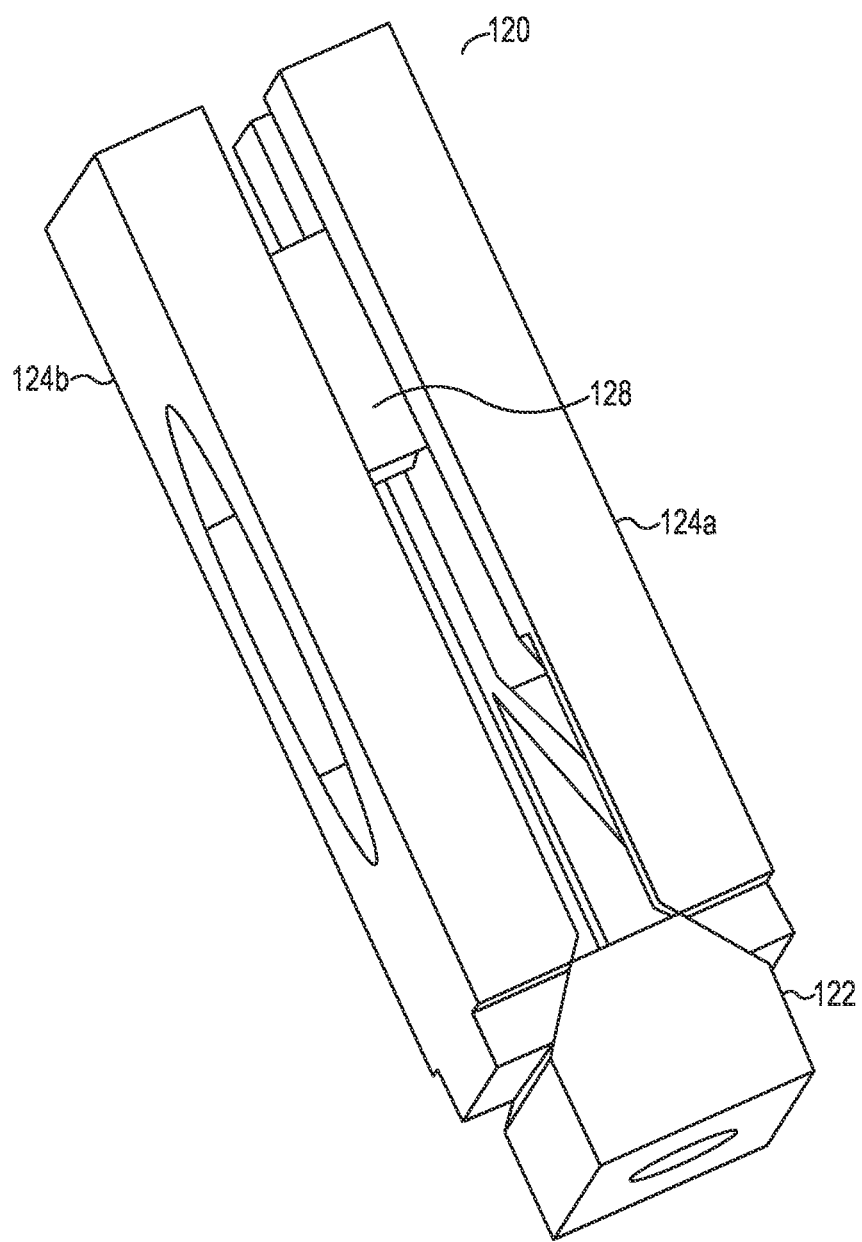
FIG. 15 depicts a perspective view of an embodiment of the present invention.

FIG. 15 depicts spacer 120 having spacer body 122 and expandable members 124a and 124b. Spacer 120 may be opened to an expanded configuration by drawing back distal ramp 128 back with a screw or other suitable mechanism.

Figure 16:
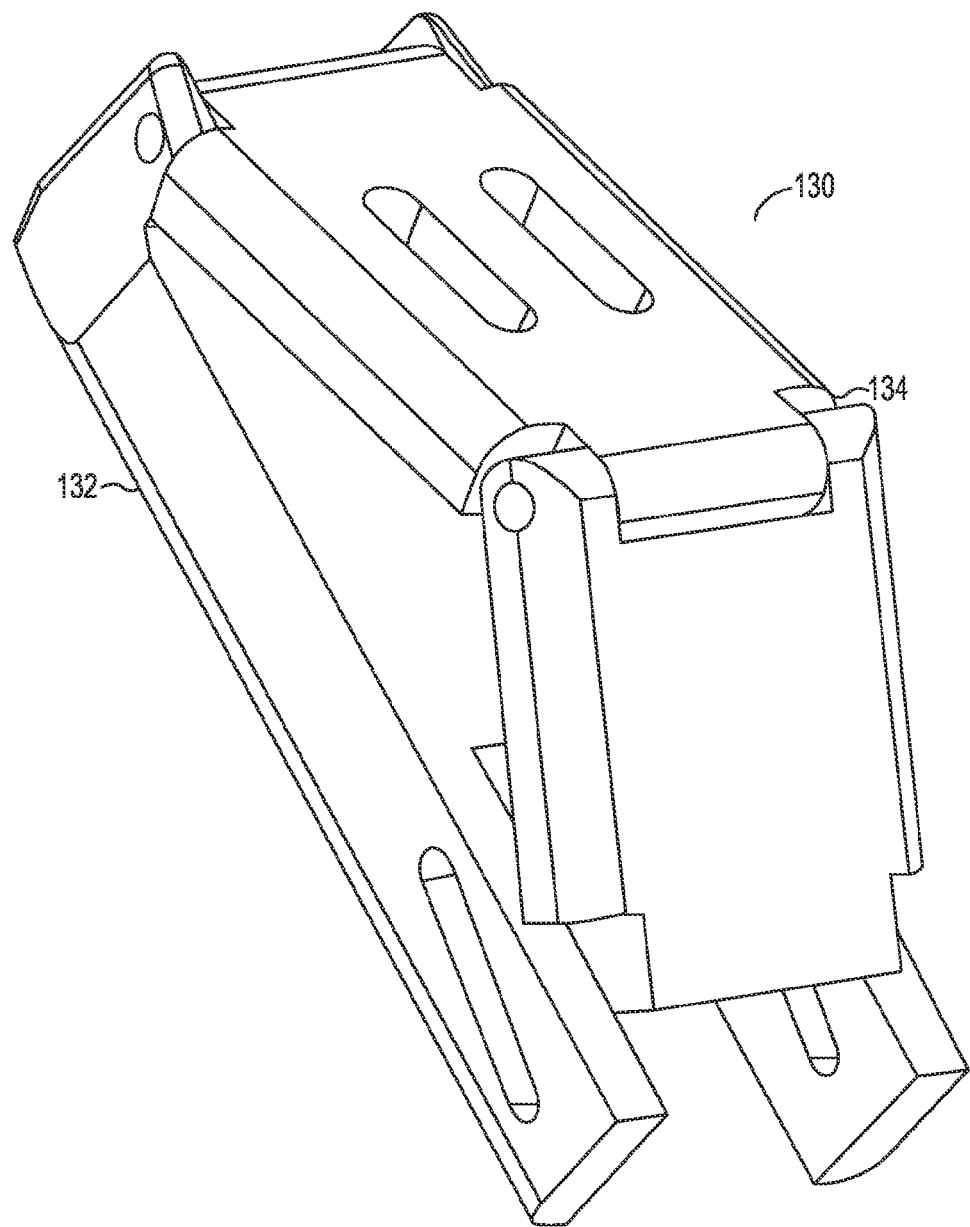
FIG. 16 depicts a perspective view of an embodiment of the present invention.

FIG. 16 depicts an embodiment of spacer 130 having spacer body 132 and expandable member 134.

Figure 17:
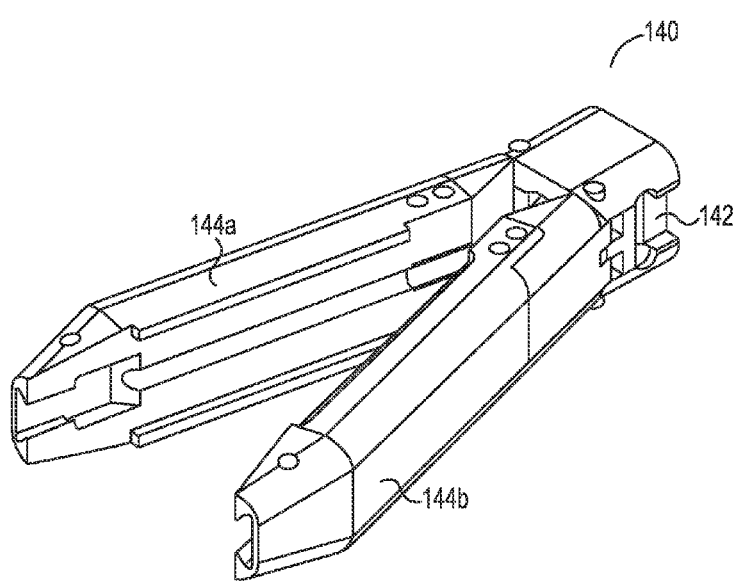
FIG. 17 depicts a perspective view of an embodiment of the present invention.

FIG. 17 depicts an embodiment of spacer 140 having spacer body 142 and expandable members 144a and 144b. Any of the embodiments of the present invention may include expandable members which may be expanded from a first closed position to a second open position, or any position therebetween, in a variety of ways. According to one aspect of the present invention, expandable members may be expanded by a mechanical expansion tool such as for example, a paddle or rod. In such an example embodiment, a mechanical expansion tool may be inserted through an opening in spacer body 142 and in between expandable members 144a and 144b. A mechanical expansion tool may then be actuated to move expandable members from a first closed position to a second open position. Expandable members 144a and 144b may be partially opened, fully opened or opened to any position therebetween.

In another embodiment, expandable members may be expanded by the introduction of a balloon. In such an example embodiment, a deflated balloon may be inserted through an opening in spacer body 142 and in between expandable members 144a and 144b. The balloon may then be inflated, moving expandable members 144a and 144b from a first closed position to a second open position. Expandable members 144a and 144b may be partially opened, fully opened or opened to any position therebetween.

In yet another embodiment, expandable members may be expanded by the introduction of fill material, such as for example bone graft, bone substitute or any biocompatible fill material or any combination thereof. Expandable members may be partially opened, fully opened or any opened to any position therebetween.

Although the description of the invention generally contemplates placing the PEEK spacer of the present invention in the intervertebral space, the PEEK spacer of the present invention may also be placed within a vertebral body.

Although the description of the invention generally contemplates using spacer comprised of PEEK, any biocompatible material or combination thereof may be used in the composition of the spacer.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. An intervertebral spacer comprising:
   a spacer body; and a first expandable member and a second expandable member, each of the first and second expandable members including a pivot end and a free end opposite the pivot end, wherein only the pivot end is pivotably attached to the spacer body at a respective first and second pivot axis, each of the first and second expandable members defining a longitudinal length dimension spanning from the pivot end to the free end, respectively, and a spacer length dimension is defined as spanning from the first pivot axis of the first expandable member to the second pivot axis of the second expandable member, wherein the intervertebral spacer is sized to be placed through Kambin's triangle, and wherein the spacer length dimension is smaller than the longitudinal length dimension of each of the first and second expandable members.

2. The spacer of claim 1 wherein the spacer includes a first closed position, a second open position and any position therebetween.

3. The spacer of claim 1 including an opening configured for bone fill material insertion.

4. The spacer of claim 1, wherein the first and second expandable members and the spacer body together define a horizontally confined bone fill material retaining space when inserted into an intervertebral disc space.

5. The spacer of claim 1 configured to allow bony ingrowth therethrough.

6. The spacer of claim 1 configured for insertion in a first position and rotation into a second implanted position.

7. A system for performing facet sparing spine surgery comprising:

a spacer, including a spacer body sized to be placed through Kambin's triangle;

a first expandable member and a second expandable member, each of the first and second expandable members including a pivot end and a free end opposite the pivot end, wherein only the pivot end is pivotably attached to the spacer at a respective first and second pivot axis, each of the first and second expandable members defining a longitudinal length dimension between the pivot end and the free end, respectively, and a spacer length dimension is defined as spanning from the first pivot axis of the first expandable member to the second pivot axis of the second expandable member; and a tool configured to move the spacer from a first closed position to a second open position, wherein the spacer length dimension is smaller than the longitudinal length dimension of each of the first and second expandable members.

8. The system of claim 7 wherein the spacer includes a first closed position, a second open position and any position therebetween.

9. The system of claim 8 wherein the tool is configured to move the spacer between the open position, the closed position and any position therebetween.

10. The system of claim 7 wherein the spacer includes an opening configured for bone fill material insertion.

11. The system of claim 7 wherein the first and second expandable members and the spacer body together define a horizontally confined bone fill material retaining space when inserted into an intervertebral disc space.

12. The system of claim 7 wherein the spacer is configured to allow bony ingrowth therethrough.

13. The system of claim 7 wherein the spacer is configured for insertion in a first position and rotation into a second implanted position.

14. An intervertebral spacer comprising:

a spacer body; and a first expandable member including a pivot end rotatably attached to the spacer body and a free end opposite the pivot end, wherein the pivot end rotates about a pivot point adjacent the pivot end and the free end sweeps through a radial arc as the first expandable member rotates about the pivot point, the at least one expandable member defining a longitudinal length dimension between the pivot end and the free end; and a second member including a first end attached to the spacer body and an unattached opposing second end, wherein the intervertebral spacer is sized to be placed through Kambin's triangle, wherein a spacer length dimension is defined as spanning from the pivot point of the first expandable member to a point where the first attached end of the second member is attached to the spacer body, and wherein the spacer length dimension is smaller than the longitudinal length dimension of the first expandable member.

15. The spacer of claim 14, wherein the first end of the second member is a pivot end rotatably attached to the spacer body and the second end is a free end opposite the pivot end, wherein the point where the first attached end of the second member is attached to the spacer body is a pivot point, wherein the pivot end rotates about the pivot point adjacent the pivot end and the free end sweeps through a radial arc as the second member rotates about the pivot point.

16. The spacer of claim 14, wherein the spacer body includes a channel defined there through and is configured to receive a mechanical expansion tool inserted through the opening which contacts at least the first expandable member to move the first expandable member into an expanded configuration.

17. The spacer of claim 14, further including an opening configured for bone fill material insertion.

18. The spacer of claim 14, wherein the first expandable member, the second member and the spacer body together define a horizontally confined bone fill material retaining space when inserted into an intervertebral disc space.

19. The spacer of claim 14, wherein the spacer is configured to allow bony ingrowth therethrough.

20. The spacer of claim 14, wherein the spacer is configured for insertion in a first position and rotation into a second implanted position.

* * * * *